United States Patent [19]

Harada

[11] Patent Number: 5,682,911
[45] Date of Patent: Nov. 4, 1997

[54] INTERPROXIMAL FLOSS BRUSH

[75] Inventor: Stephen D. Harada, Piedmont, Calif.

[73] Assignee: The Megan Sumi Corporation, Piedmont, Calif.

[21] Appl. No.: 658,488

[22] Filed: Jun. 10, 1996

[51] Int. Cl.[6] ..................................... A61C 15/00
[52] U.S. Cl. ................................................ 132/321
[58] Field of Search ............................. 132/308, 309, 132/310, 321, 323, 324, 325, 326, 327, 328, 329; 15/167.1

[56] References Cited

U.S. PATENT DOCUMENTS

| | | | |
|---|---|---|---|
| 3,896,824 | 7/1975 | Thornton | 132/89 |
| 4,008,727 | 2/1977 | Thornton | 132/321 |
| 4,277,297 | 7/1981 | Thornton | 156/161 |
| 4,280,518 | 7/1981 | Gambaro | 132/93 |
| 4,911,187 | 3/1990 | Castillo | 132/321 |
| 4,922,936 | 5/1990 | Buzzi et al. | 132/329 |
| 5,063,948 | 11/1991 | Lloyd | 132/321 |
| 5,125,424 | 6/1992 | Eisen | 132/323 |
| 5,284,169 | 2/1994 | Gilligan et al. | 132/321 |
| 5,311,890 | 5/1994 | Thornton | 132/329 |

FOREIGN PATENT DOCUMENTS

| | | | |
|---|---|---|---|
| 0361120 | 4/1990 | European Pat. Off. | 15/167.1 |
| 2677537 | 12/1992 | France | 132/321 |
| 3015686 | 8/1993 | WIPO | 132/321 |

OTHER PUBLICATIONS

Henry Schein brochure, entitled "Get These Outstanding Products By Advanced Implant Technologies Today!," single 2-sided page; undated.

*Primary Examiner*—Cary E. O'Connor
*Attorney, Agent, or Firm*—Holland & Knight LLP

[57] ABSTRACT

A dental hygiene device for cleaning enlarged embrasures includes a brush portion having a plurality of bristles projecting from a rigid spine opposed ends of which are secured to lengths of flexible filament such as dental floss. A free end of at least one of the filaments may be provided with a stiff pin-like tip useful as a toothpick or in threading the device through gaps between teeth or orthodontic structures.

5 Claims, 2 Drawing Sheets

INTERPROXIMAL FLOSS BRUSH

FIELD OF THE INVENTION

The invention relates to dental hygiene devices which are especially useful for cleaning those portions of teeth, dental prosthesis, or orthodontic work lying adjacent spaces or gaps such as enlarged gaps between neighboring teeth. More particularly the present invention relates to dental hygiene devices including a relatively small diameter brush having short bristles extending from a rigid central spine each end of which is attached to a length of flexible filament such as dental floss or dental tape.

BACKGROUND OF THE DISCLOSURE

In addition to regular dental checkups and periodic professional cleaning of the teeth to remove plaque, a regular personal regimen of dental hygiene is essential to maintaining the health and appearance of the teeth and gums. The use of a manual toothbrush having an array of bristles mounted near one end of some form of handle is the most familiar and commonly-used implement for this purpose. Also known are various forms of mechanized brushing devices in which energy in various forms are imparted to the bristles in various other ways including electro-mechanical drives which cause tufts of bristles to rotate either unidirectionally or biodirectionally in an oscillatory fashion. Toothbrushes in which ultrasonic energy is imparted to bristles are also known in the art. The foregoing types of toothbrushes can usually be selected from a range of bristle stiffness ranging from relatively stiff or "hard" to relatively compliant or "soft".

Toothbrushes of the types described above are effective for cleaning most areas of the teeth, dental prosthesis, and orthodontic appliances but have significant limitations. These limitations stem mainly for the need of these devices for some form of a relatively long and rigid or semi-rigid handle and the fact that bristles, by their nature, clean most effectively when they extend substantially perpendicularly to the surface being cleaned. Given the positioning and movement constraints imposed by using devices having such handles within the confines of a human mouth, it is simply not possible to position the brush and move its bristles so that maximally effective cleaning can be realized over all areas of the teeth, dental work and gums. These disadvantages have been ameliorated somewhat by various improvements directed toward improving the maneuverability of toothbrush heads such as making the heads smaller, angling the brush handle, providing a flexible joint in the handle and arranging bristles of varying lengths to form tufts having special contours intended to improve their penetration of irregularly shaped structures. These solutions however, are not entirely sufficient to effectively clean all areas especially those adjacent spaces or gaps such as those present between teeth, especially when root surfaces are exposed.

An alternative to brushing which is claimed to be effective for cleaning teeth both above and below the gum line as well as for dislodging foreign matter from between teeth involves the use of devices which operate by projecting a stream of water or other fluid either continuously or in a rapidly pulsating manner. Like many of the mechanically-powered toothbrushes, these devices tend to be relatively expensive and require a power source. They also require a fluid supply and cannot be used effectively with toothpaste. Since these devices tend to be most effective when the fluid stream is directed normally to the surface to be cleaned, their effectiveness for cleaning between teeth is limited.

It has been both well known and widely recommended to use a flexible filament such as dental floss or dental tape to remove food or other foreign matter from the gaps between teeth both above and below the gumline. Dental floss is easy to use, can be coated with a wax or other substance to ease its insertion between teeth and can be colored, flavored and/or impregnated with beneficial fluoride compounds. While flossing is effective for removal of foreign matter as well as stimulation of gum tissues, it is not, however, thought to be as effective as brushing in removing plaque and staining. Flossing continues to be a well-recommended practice and indeed may still be the only practical way of cleaning the area between teeth which are tightly spaced and will therefore not allow for insertion of other devices.

An alternative or adjunct to flossing, where interproximal spacing permits it, involves use of an interdental brush such as the type available from Butler under the trademark Proxabrush®. That product takes the form of a small replaceable brush head mounted on a reusable handle. The brush head is formed of a twisted wire spine which defines a central axis from which bristles extend radially outward. In a similar device having a permanent handle, such as that shown in U.S. Pat. No. 4,280,518 to Gambaro, the bristles are of equal length to form a cylindrical array. In another form, the bristle array is tapered in a generally conical shape with the shortest of the bristles being located near the free end of the wire spine to facilitate their insertion between teeth. Handle-mounted interproximal brushes can be used either with or without a dentifrice, are relatively inexpensive and do an effective job of brushing where they can be inserted between teeth from the outer or cheek-facing side of the teeth. However, due to their handles, these devices can be difficult to insert and manipulate properly from the inside (lingual side) of the teeth and can consequently be less effective in cleaning those areas.

Attempts have been made in the prior art to enhance the cleaning capabilities of dental floss by providing it with bristles. U.S. Pat. No. 5,063,948 to Lloyd for example discloses a dental floss having bristled segments defined by a series of radially outwardly projecting bristles. U.S. Pat. Nos. 3,896,824; 4,277,297 and 5,311,890, all to Thornton, disclose string-like tooth cleaning elements having enlarged, spongy portions formed of numerous crimped and crinkled fibers fused to one another at various points. These spongy portions can be drawn through interproximal spaces for cleaning them as well as areas in and around bridges, implants and orthodontic appliances. These devices all retain the advantages of dental floss and, due to their flexibility and lack of a rigid handle, can be inserted and manipulated with relative ease. They too, however, suffer from some significant limitations. To appreciate these limitations, some mechanics of bristle action must be considered.

Bristles clean most effectively when their tips engage the surface being cleaned under a force that lies within a particular range of forces that is related to the stiffness of the bristles. If the force is not great enough, the bristle tips will not engage the surface being cleaned with sufficient pressure to do as effective a job of cleaning as possible. On the other hand, if the force is too great, the bristles will bend so as to engage the surface being cleaned with their sides rather than their tips. This also results in less than optimal cleaning. It is for that reason that toothbrushes are routinely discarded and replaced when their bristles become bent or flattened near their tips.

With the above background, the limitations of the structures disclosed in the Lloyd and Thornton patents can be understood. Because of the flexibility of the structure to which they are affixed, the bristles or spongy fibers of these devices will tend to simply wipe tooth surfaces with their sides rather than forcibly engage them with their tips as they are drawn through interproximal spaces. This will tend to occur because the flexible filament structure from which the bristles protrude will tend to move away from the tooth surface in response to the reaction force generated by contact of the bristle with the tooth. As the interproximal spaces between teeth become larger, such as in patients with receded gums or where gum surgery has been performed, the limitations become increasingly more pronounced. Pulling the floss taut, in an attempt to overcome this effect is not only difficult in light of the space limitations inside the mouth, but would also be risky due to the possibility of cutting the gums with the filament.

SUMMARY OF THE INVENTION

In view of the limitations of the prior art described above, it is an object of the invention to provide a dental hygiene device which cannot only be used as a dental floss but which can be used to (clean) teeth, roots, gingiva, and under and around dental prothesis, and orthodontic structures adjacent enlarged embrasures with efficacy comparable to that of an interproximal brush mounted on a handle but which does not include a rigid handle and is therefore capable of being easily used to effectively clean areas adjacent the lingual side of such structures as well as those adjacent the cheeks.

It is a further object of the invention to provide a device which fulfills the foregoing objective while being capable of being used either with or without a dentifrice.

Another object of the invention is to fulfill the foregoing objects by providing a device that has a simple structure which can be manufactured and sold at low cost.

The present invention meets the foregoing objectives by providing a new and improved interproximal floss brush which includes at least one bristled brush segment having a plurality of surrounding bristles anchored at their bases, to a rigid longitudinal spine whose opposing free ends are each secured to a length of flexible filament of dental floss, nylon or other suitable material. The filament can be used like conventional dental floss and serves as a thin flexible lead which can be inserted readily into gaps such as enlarged proximal spaces and used to pull the brush portion back and forth therethrough. Unlike prior art devices in which bristles project from a compliant filament, the invention contemplates anchoring the bases of the bristles to a spine which is substantially more rigid than the bristles themselves. The bristles located on opposing sides of an interproximal gap support the spine permitting it to serve as a mechanical supporting base capable of generating reaction forces opposing the forces tending to push the tips of the bristles away from the surface being cleaned. In this way, the invention provides a cleaning action which is significantly more effective than that which has been possible with bristled flosses of the prior art. Since the filaments affixed to the brush portion permit insertion from either the cheek side or the lingual side of the teeth, the brush portion can easily be passed repeatedly through gaps in a bidirectional reciprocating manner to clean both the gingival side and lingual side of structures with substantially equal efficacy. The invention can also be used with or without a dentifrice, is simple to use and can be manufactured and sold at low cost. According to a further aspect of the invention, one or both free ends of the flexible filament may be provided with a thin, stiff tip useful as a toothpick and/or to facilitate threading the device through gaps, dental prosthesis or orthodontic appliances.

These and other objects and advantages of the present invention will become even more clear to persons of ordinary skill in light of the following detailed description and the appended drawings in which like reference numerals designate like items.

DETAILED DESCRIPTION OF THE INVENTION

Figure 1:
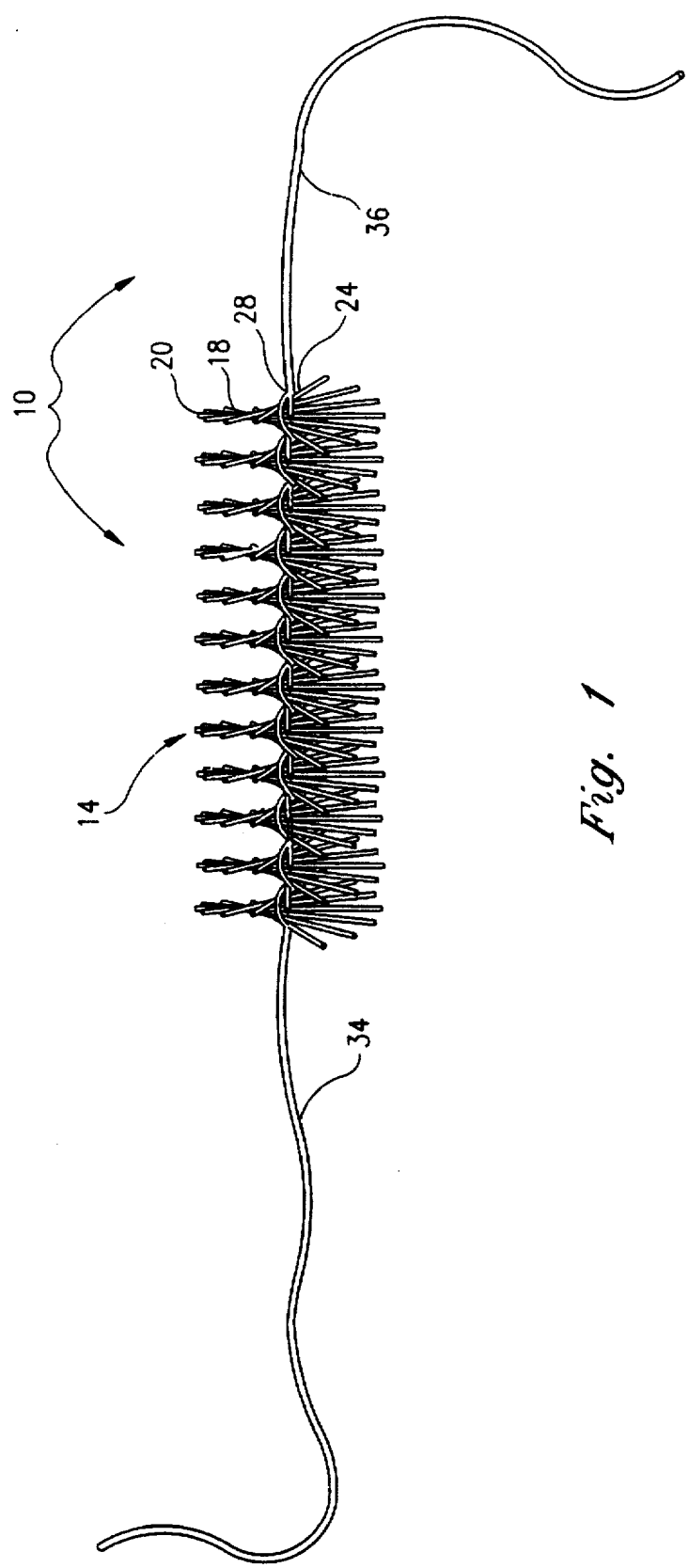
FIG. 1 is a perspective view of a preferred embodiment of a floss brush constructed according to the invention.

FIG. 1 shows a preferred embodiment of an interproximal floss brush 10 constructed according to the invention. Floss brush 10 includes a small brush 14 which is preferably about 7.5 millimeters in length. Brush 14 includes a plurality of bristles 18 each of which has a free end or tip 20 and a base portion 24 secured to a rigid spine 28 which extends along the entire length of brush 14. Spine 28 has opposing ends to which are firmly secured, by tying, adhesive, bonding or otherwise, a pair of flexible filaments 34 and 36 which are each preferably about five to ten inches in length.

Filaments 34 and 36 are preferably about 0.3 millimeters in diameter but may range in overall diameter from about 0.2 millimeters to about 0.5 millimeters and may be formed of single or multiple fibers of material with ordinary waxed or unwaxed dental floss or dental tape being preferred materials. Alternatively, filaments 34 and 36 may be formed of nylon, polyester or various other synthetic materials or blends thereof capable of being sanitized or sterilized without undue loss of strength or flexibility.

Bristles 18 may suitably be formed of nylon, polyester or other materials known in the art for use as toothbrush bristles and are preferably of a diameter ranging from about 0.04 millimeters to about 0.1 millimeters, and a length, as measured from tip 20 to base 24, ranging from about 2.0 millimeters to about 4.0 millimeters with about 3.25 millimeters being preferred. Although bristles 18 can be of any desired stiffness, ones having a stiffness regarded as "soft" in conventional toothbrushes are ordinarily preferred so as to provide effective cleaning while avoiding undue abrasion or irritation of soft gingival tissue or roots of the teeth. In the embodiment shown in FIG. 1 bristles 18 are all of substantially equal length with each extending substantially radially outwardly from spine 28 so as to define a substantially right cylindrical shaped bristle array. Arrays of bristles in other forms may also be used.

Spine 28 may suitably be formed of a variety of materials using a variety of techniques. In a preferred form, spine 28 is formed of a length of wire of stainless steel or a mild steel having a thin corrosion-resistant coating of polytetrafluoroethyene (Teflon®), polyvinylchloride (PVC) or other suitable material and having an overall thickness of about 0.25 millimeters. To form spine 28, a length of such wire may be folded back on itself and twisted together to capture and secure bristles 18 thereto in the conventional manner used in the fabrication of bottle brushes, test tube brushes and gun cleaning brushes. This construction provides brush 14 with sufficient rigidity to maintain the tips 20 of bristles 18 in effective cleaning engagement with the surfaces of teeth or other structures rather than yielding under the net spring force exerted on spine 28 by bristles 18.

Figure 2:
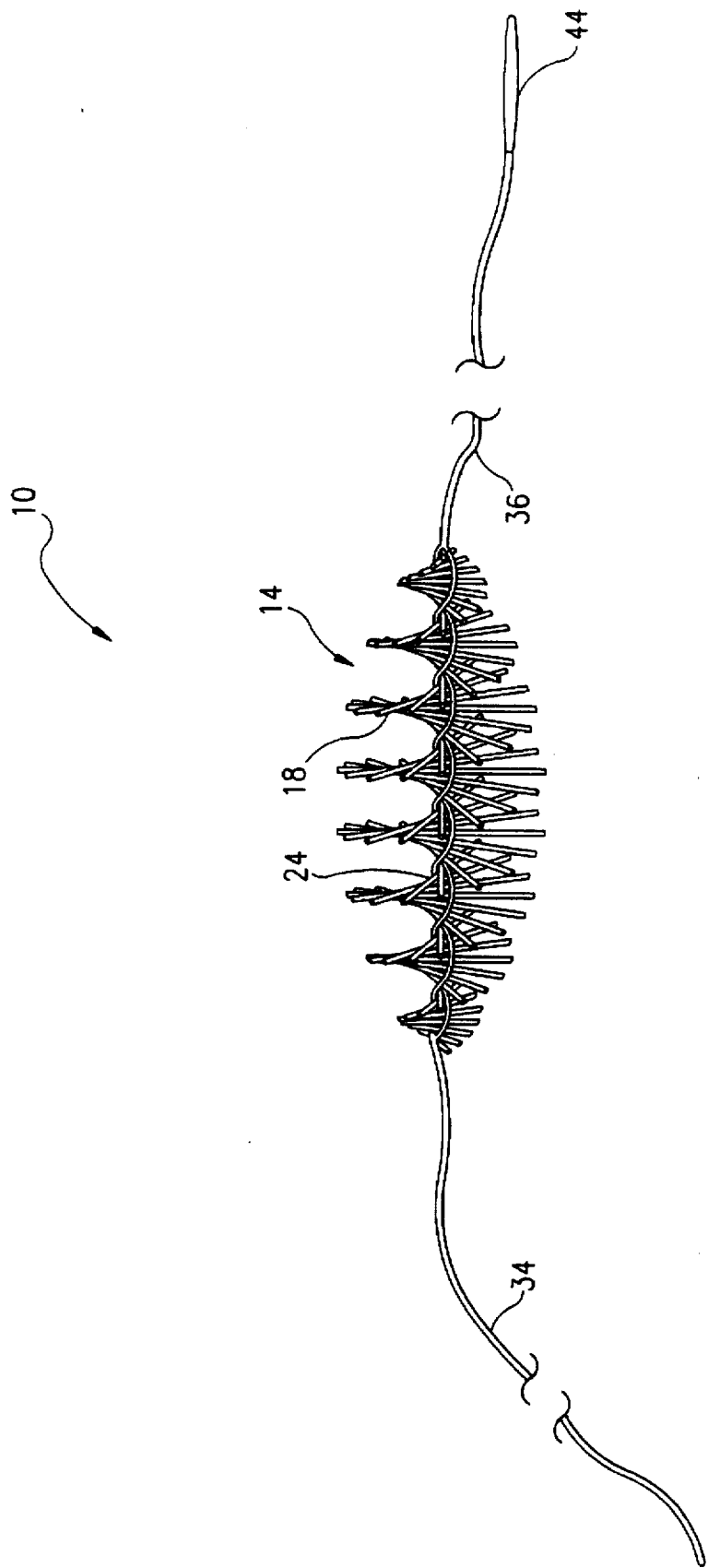
FIG. 2 is a perspective view of an alternative embodiment of a floss brush constructed according to the present invention.

FIG. 2 depicts an alternate embodiment of a floss brush 14 constructed according to the invention and which is similar to the embodiment of FIG. 1 except as noted. In the embodiment of FIG. 2 a free end of at least one end of one of filaments 34 or 36 is straightened and stiffened for a length of approximately 100 to 150 millimeters to form a pin-like projection or tip 44 which can be used either in the manner of a toothpick or as a guide to facilitate threading floss brush 14 through spaces or between gaps. Tip 44 may suitably be formed by melting the end portion of filament 34 or 36 where same is made of nylon or other suitable thermoplastic material. Alternatively, a free end of filament 34 or 36 may be impregnated or coated with a hardenable liquid material such as an epoxy or a molten thermoplastic.

Unlike the embodiment of FIG. 1 which shows bristles 18 of constant length dispersed in a more or less uniform density surrounding spine 28, the base portions 24 of the bristles 18 in the embodiment of FIG. 2 are arranged to wind around spine 28 in a spiral pattern so that bristles 18 extend outwardly therefrom in a helical array. It is also possible to vary the lengths of bristles 18 along the length of spine 28 to provide brush 14 with a desired contour. As FIG. 2 illustrates, bristles 18 can be arranged to progressively decrease in length so as to taper from the full length noted above near the central region of spine 28 to a much shorter dimension near one or both ends of spine 28. This provides brush 18 with a conical shape which facilitates guiding brush 18 into interproximal spaces and permits at least partial cleaning of smaller gaps where full insertion of brush 18 may not be possible.

In use, one of the filaments 34 or 36 is inserted through a space or gap to be cleaned. This can be performed by pulling a mid portion of filament 34 or 36 through the space or by threading a free end through either with or without the aid of tip 44. One or both of filaments 34 and/or 36 are then grasped by hand and pulled to draw brush 14 first in one direction through the gap and then back through in the opposite direction. This procedure is preferably performed several times, with or without a dentifrice, to effectively clean the gums and surfaces of the teeth including any exposed root areas lying adjacent to enlarged interproximal spaces. This procedure is preferably followed or preceded by use of a conventional rigid handled toothbrush with a fluoride containing dentifrice.

While the foregoing describes particular preferred embodiments of the invention, it is to be understood that the invention is not limited thereto and that in light of the present disclosure various alternative constructions will be apparent to persons skilled in the art. Accordingly, it is to be recognized that changes can be made without departing from the scope of the invention as particularly pointed out and distinctly claimed in the appended claims including all legal equivalents.

What is claimed is:

1. A dental hygiene device, comprising:

(a) a brush having a rigid spine having opposed ends and a plurality of bristles each having a base portion secured to said spine, and (b) a flexible filament secured to each said opposed end of said spine.

2. The dental hygiene device of claim 1 wherein said filament is a filament of dental floss.

3. The dental hygiene device of claim 1, wherein at least one said filament includes a free end terminating in a stiff tip.

4. The dental hygiene device of claim 1 wherein said bristles are disposed in a helical array about said spine.

5. The dental hygiene device of claim 1 wherein said bristles decrease in length to form a generally conical taper adjacent at least one of said opposed ends of said spine.

* * * * *

UNITED STATES PATENT AND TRADEMARK OFFICE
CERTIFICATE OF CORRECTION

PATENT NO. : 5,682,911

DATED : November 4, 1997

INVENTOR(S) : Stephen D. Harada

It is certified that error appears in the above-identified patent and that said Letters Patent is hereby corrected as shown below:

Column 6, line 21, in claim 1, "brash" should be --brush--

Signed and Sealed this

Twenty-seventh Day of January, 1998

Attest:

BRUCE LEHMAN

*Attesting Officer*    *Commissioner of Patents and Trademarks*